(12) United States Patent
Sakai et al.

(10) Patent No.: US 9,169,330 B2
(45) Date of Patent: Oct. 27, 2015

(54) HYBRIDOMA PRODUCING ANTI-METHYLATED DNA ANTIBODY AND UTILIZATION OF SAME

(75) Inventors: Ayako Sakai, Kobe (JP); Masahiro Kajita, Kobe (JP)

(73) Assignee: SYSMEX CORPORATION, Hogan (JP)

(*) Notice: Subject to any disclaimer, the term of this patent is extended or adjusted under 35 U.S.C. 154(b) by 757 days.

(21) Appl. No.: 13/430,295

(22) Filed: Mar. 26, 2012

(65) Prior Publication Data

US 2012/0184719 A1  Jul. 19, 2012

Related U.S. Application Data

(63) Continuation of application No. PCT/JP2010/066847, filed on Sep. 28, 2010.

(30) Foreign Application Priority Data

Sep. 28, 2009 (JP) ................................. 2009-222893
Dec. 28, 2009 (JP) ................................. 2009-298213

(51) Int. Cl.
*C07K 16/18* (2006.01)
*C07H 1/06* (2006.01)
*C12N 5/16* (2006.01)
*C07K 16/44* (2006.01)
*G01N 33/53* (2006.01)

(52) U.S. Cl.
CPC ................ *C07K 16/44* (2013.01); *C12N 5/163* (2013.01); *G01N 33/5308* (2013.01)

(58) Field of Classification Search
None
See application file for complete search history.

(56) References Cited

U.S. PATENT DOCUMENTS

| | | |
|---|---|---|
| 2003/0125292 A1 | 7/2003 | Semple et al. |
| 2004/0009943 A1 | 1/2004 | Semple et al. |
| 2004/0009944 A1 | 1/2004 | Tam et al. |
| 2004/0013649 A1 | 1/2004 | Tam et al. |
| 2009/0221066 A1* | 9/2009 | Shiota et al. .................. 435/345 |

FOREIGN PATENT DOCUMENTS

| | | |
|---|---|---|
| CN | 101124338 A | 2/2008 |
| JP | 2003-125766 A | 5/2003 |
| JP | 2005-532315 A | 10/2005 |
| WO | 2006056478 A1 | 6/2006 |
| WO | 2007139373 A1 | 12/2007 |

OTHER PUBLICATIONS

International Search Report of PCT/JP2010/066847, dated Dec. 7, 2010.
Deobagkar, D. N., et al., "Separation of 5-methylcytosine-rich DNA using immobilized antibody", Enzyme Bicrob. Technol., Feb. 1986, pp. 97-100, vol. 8.
Mizugaki M., et al., "Preparation of a Monoclonal Antibody Specific for 5-Methyl-2'-deoxycytidine and Its Application for the Detection of DNA Methylation Levels in Human Peripheral Blood Cells," Biological & Pharmaceutical Bulletin, vol. 19, No. 12, pp. 1537-1540 (Jan. 1996).
Sorensen A., et al., "Immunoprecipitation of Methylated DNA", Methods in Molecular Biology, vol. 567, pp. 249-262 (Aug. 2009).
Jacinto F., et al., "Methyl-DNA immunoprecipitation (MeDIP): Hunting down the DNA methylome," Biotechniques, vol. 44, No. 1, pp. 37, 39 (Jan. 2008).

* cited by examiner

*Primary Examiner* — Sharon Wen
(74) *Attorney, Agent, or Firm* — Sughrue Mion, PLLC

(57) ABSTRACT

The present invention relates to a hybridoma producing an anti-methylated DNA antibody, obtained by cell fusion of an antibody-producing cell obtained from an animal immunized with an antigen containing 5'-(5-methyl-2'-deoxycytidine-3'-phospho)-2'-deoxyguanosine 3'-phosphate with a myeloma cell. The present invention also relates to a monoclonal antibody produced by the hybridoma and a method for immunoprecipitation of a methylated DNA using the antibody.

2 Claims, 5 Drawing Sheets

SEQUENCE LISTING

```
<160> NUMBER OF SEQ ID NOS: 14

<210> SEQ ID NO 1
<211> LENGTH: 18
<212> TYPE: DNA
<213> ORGANISM: Artificial Sequence
<220> FEATURE:
<223> OTHER INFORMATION: primer

<400> SEQUENCE: 1
gaggccttcg ctggagtt                                                 18

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
gtactcactg gtggcgaaga                                               20

<210> SEQ ID NO 3
<211> LENGTH: 25
<212> TYPE: DNA
<213> ORGANISM: Artificial Sequence
<220> FEATURE:
<223> OTHER INFORMATION: primer

<400> SEQUENCE: 3
ggaggagtca agagaagttg gaagc                                         25

<210> SEQ ID NO 4
<211> LENGTH: 23
<212> TYPE: DNA
<213> ORGANISM: Artificial Sequence
<220> FEATURE:
<223> OTHER INFORMATION: primer

<400> SEQUENCE: 4
```

```
cccacactcc atttccattc ctc                                           23
```

<210> SEQ ID NO 5
<211> LENGTH: 22
<212> TYPE: DNA
<213> ORGANISM: Artificial Sequence
<220> FEATURE:
<223> OTHER INFORMATION: primer

<400> SEQUENCE: 5

```
gagaagtagt tggaaggaga gg                                            22
```

<210> SEQ ID NO 6
<211> LENGTH: 30
<212> TYPE: DNA
<213> ORGANISM: Artificial Sequence
<220> FEATURE:
<223> OTHER INFORMATION: primer

<400> SEQUENCE: 6

```
ccctacacta actacaataa tttaatatcc                                    30
```

<210> SEQ ID NO 7
<211> LENGTH: 25
<212> TYPE: DNA
<213> ORGANISM: Artificial Sequence
<220> FEATURE:
<223> OTHER INFORMATION: primer

<400> SEQUENCE: 7

```
gtaggatggt ttggatttgg ggtaa                                         25
```

<210> SEQ ID NO 8
<211> LENGTH: 29
<212> TYPE: DNA
<213> ORGANISM: Artificial Sequence
<220> FEATURE:
<223> OTHER INFORMATION: primer

<400> SEQUENCE: 8

```
caactactcc taactctata aactaccaa                                     29
```

<210> SEQ ID NO 9
<211> LENGTH: 19
<212> TYPE: DNA
<213> ORGANISM: Artificial Sequence
<220> FEATURE:
<223> OTHER INFORMATION: primer

<400> SEQUENCE: 9

```
ggaaacagct atgaccatg                                                19
```

<210> SEQ ID NO 10
<211> LENGTH: 193
<212> TYPE: DNA
<213> ORGANISM: Homo sapiens

<400> SEQUENCE: 10

```
ggaggagtca agagaagttg gaagccaact gagagagagg gaaggcttga agtggtcagg   60
acagtgaaca cctaagagac atccactgaa tttgcccact aggaagccat tagtgacttc  120
aataggaaca tcttcagtgc atcatgaagg ccaaagattg ccatgaaaga gaggaatgga  180
aatggagtgt ggg                                                     193
```

```
<210> SEQ ID NO 11
<211> LENGTH: 73
<212> TYPE: DNA
<213> ORGANISM: Artificial Sequence
<220> FEATURE:
<223> OTHER INFORMATION: oligonucleotides
<220> FEATURE:
<221> NAME/KEY: modified_base
<222> LOCATION: (20)..(20)
<223> OTHER INFORMATION: m5c
<220> FEATURE:
<221> NAME/KEY: modified_base
<222> LOCATION: (34)..(34)
<223> OTHER INFORMATION: m5c
<220> FEATURE:
<221> NAME/KEY: modified_base
<222> LOCATION: (52)..(52)
<223> OTHER INFORMATION: m5c

<400> SEQUENCE: 11
cgaggtcgac ggtattgatc gagtatcgat agtcgatatc gatatcgata tcgatataca    60
acgtcgtgac tgg                                                       73

<210> SEQ ID NO 12
<211> LENGTH: 73
<212> TYPE: DNA
<213> ORGANISM: Artificial Sequence
<220> FEATURE:
<223> OTHER INFORMATION: oligonucleotides
<220> FEATURE:
<221> NAME/KEY: modified_base
<222> LOCATION: (20)..(20)
<223> OTHER INFORMATION: m5c
<220> FEATURE:
<221> NAME/KEY: modified_base
<222> LOCATION: (34)..(34)
<223> OTHER INFORMATION: m5c
<220> FEATURE:
<221> NAME/KEY: modified_base
<222> LOCATION: (52)..(52)
<223> OTHER INFORMATION: m5c

<400> SEQUENCE: 12
cgaggtcgac ggtattgatc tagtatcgat agtctatatc gatatcgata tctatataca    60
acgtcgtgac tgg                                                       73

<210> SEQ ID NO 13
<211> LENGTH: 15
<212> TYPE: DNA
<213> ORGANISM: Artificial Sequence
<220> FEATURE:
<223> OTHER INFORMATION: primer

<400> SEQUENCE: 13
cgaggtcgac ggtat                                                     15

<210> SEQ ID NO 14
<211> LENGTH: 17
<212> TYPE: DNA
<213> ORGANISM: Artificial Sequence
<220> FEATURE:
<223> OTHER INFORMATION: primer

<400> SEQUENCE: 14
ccagtcacga cgttgta                                                   17
```

HYBRIDOMA PRODUCING ANTI-METHYLATED DNA ANTIBODY AND UTILIZATION OF SAME

CROSS-REFERENCE TO RELATED APPLICATION

This is a continuation of International Application of PCT/JP2010/066847 with an international filing date of Sep. 28, 2010, now abandoned.

BACKGROUND OF THE INVENTION

1. Field of the Invention

The present invention relates to hybridomas producing anti-methylated DNA antibodies, monoclonal antibodies produced by the hybridomas and a method for immunoprecipitation of methylated DNA by using the antibodies.

2. Description of the Related Art

Chromosome DNAs of higher eukaryotes may sometimes undergo methylation at the 5-position of C (cytosine) among other bases constituting DNAs. Such DNA methylation in higher eukaryotes functions as a mechanism for suppression of expression of genetic information. For example, when a region containing many CpGs (also referred to as CpG islands), which is often found in promoter regions of certain genes, is methylated, transcription of these genes may be suppressed. On the other hand, when a CpG island is not methylated, a transcription factor can bind to the promoter region and the gene can be transcribed.

Accordingly, DNA methylation is one of control mechanisms of gene expression. DNA methylation plays important roles in various physiological and pathological phenomena such as early embryonic development, expression of tissue specific genes, genomic imprinting and X chromosome inactivation which are characteristic to mammals, stabilization of chromosomes, synchronization of DNA replication and the like.

Recently, it has also been revealed that DNA methylation is deeply involved in cancers or other diseases. Thus, studies have been carried out on confirmed diagnosis or prognostic prediction of cancer based on methylation analysis of various genes.

One of the known techniques for recovery of methylated DNA is Methylated DNA Immunoprecipitaion (MeDIP method). According to the MeDIP method, methylated DNA is immunoprecipitated with an antibody specifically recognizing methylated DNA or with a methylated DNA-binding protein, thereby concentrating methylated DNA in a sample. It has also been known that the MeDIP method can be combined with microarray analysis and the thus combined MeDIP-chip method can be used for exhaustive analysis of DNA methylation status.

Various anti-methylated DNA antibodies to be used in the MeDIP method have been commercially available, among which antibodies recognizing 5-methyl cytosine or 5-methyl cytidine have been frequently used, for example. Japanese Unexamined Patent Application Publication No. 2003-125766 discloses that 5-methyl-2'-deoxycytidine is used as an antigen to generate hybridomas from which a monoclonal antibody is obtained and the antibody may be used in enzyme-linked immunosorbent assay (ELISA) to quantify 5-methyl-2'-deoxycytidine.

SUMMARY OF THE INVENTION

When DNAs obtained by the MeDIP method are analyzed for their methylation, it is preferred that the MeDIP method using an anti-methylated DNA antibody can provide high recovery amount and concentrating ratio of methylated DNA.

However, when the anti-methylated DNA antibody used has low binding ability or is used in the MeDIP method on a sample having a low DNA content, methylated DNA may not be recovered with a necessary and sufficient amount for methylated DNA analysis, thereby decreasing the sensitivity of the analysis. When the anti-methylated DNA antibody has low specificity and is used in the MeDIP method, the obtained DNA may include high amount of unmethylated DNA, thereby deteriorating reliability of methylated DNA analysis.

Accordingly, there is a need for developing an anti-methylated DNA antibody having superior binding ability and specificity for methylated DNA, in order to further improve the recovery amount and concentrating ratio of methylated DNA in the MeDIP method.

In view of the above circumstances, an objective of the present invention is to provide a hybridoma producing an anti-methylated DNA antibody having superior binding ability and specificity for methylated DNA.

Another object of the present invention is to provide an anti-methylated DNA antibody which allows a MeDIP method that can provide high recovery amount and concentrating ratio of methylated DNA.

Further object of the present invention is to provide a MeDIP method that can provide high recovery amount and concentrating ratio of methylated DNA by using the anti-methylated DNA antibody.

The present inventors noted of the use of 5'-(5-methyl-2'-deoxycytidine-3'-phospho)-2'-deoxyguanosine 3'-phosphate (hereinafter also referred to as "5-methyl-dCpdGp") represented by the following formula (I):

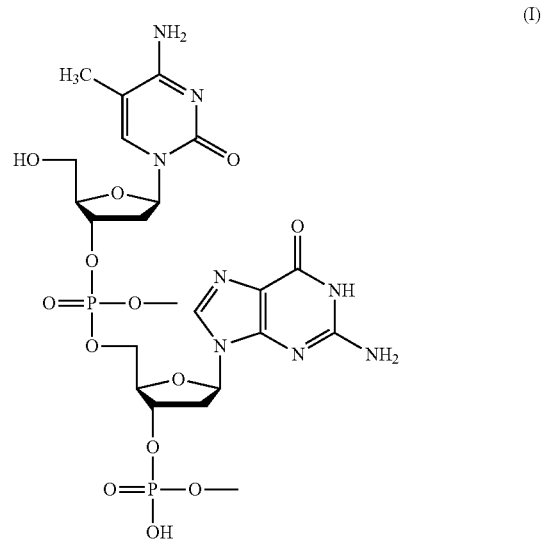

as an antigen. The present inventors have found that anti-methylated DNA antibodies having superior binding ability and specificity for methylated DNA can be obtained from hybridomas obtained by immunizing an animal with an antigen containing 5-methyl-dCpdGp, and fusing antibody-producing cells from the animal with myeloma cells to generate hybridomas. Accordingly, the present inventors have achieved the present invention.

Thus, the present invention provides the hybridoma (hereinafter also referred to as "the present hybridoma") obtained by fusing antibody-producing cells obtained from an animal immunized with 5-methyl-dCpdGp with myeloma cells.

The present invention also provides a monoclonal antibody produced by the hybridoma and a method for immunoprecipitation of methylated DNA using the antibody.

The present hybridoma can provide the anti-methylated DNA antibody having superior binding ability and specificity for methylated DNA, in particular, a methylated CpG sequence. When the obtained antibody is used in the MeDIP method, recovery amount and concentrating ratio of methylated DNA can be increased compared to a method using the conventional anti-methylated DNA antibody.

DETAILED DESCRIPTION OF THE EMBODIMENTS

Figure 1:
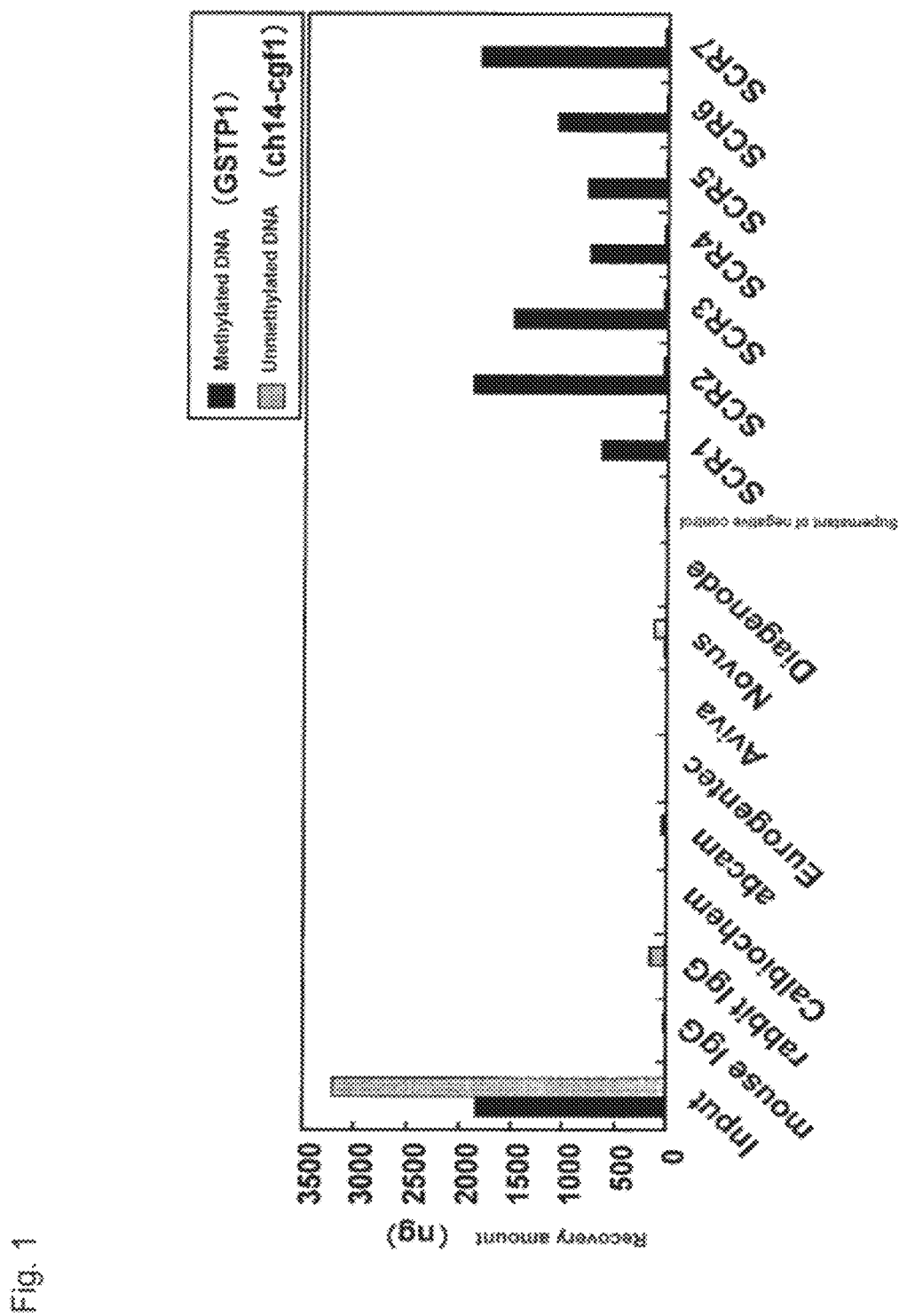
FIG. 1 is a bar graph showing the amounts of methylated DNA and unmethylated DNA recovered by the MeDIP method using the culture supernatants of the present hybridomas and various commercial antibodies.

As used herein, a "CpG sequence" means a sequence in a base sequence in which a cytosine (C) and a guanine (G) are adjacent in this order from 5' to 3'. Similarly, a "CpT sequence" means a sequence in a base sequence in which C and thymine (T) are adjacent in this order from 5' to 3'. The letter "p" in "CpG" and "CpT" represents a phosphodiester bond between C and G or T.

A "methylated CpG sequence" means a CpG sequence which is methylated at the 5-position of cytosine. It is known that the 5-position of cytosine in a site containing a CpG sequence is methylated in mammal genomic DNA.

A "hybridoma" means a hybrid cell obtained by artificially fusing an antibody-producing cell such as a lymphocyte and a myeloma cell, and it can be cultured and has antibody-producing ability.

As used herein, the "concentrating ratio" of methylated DNA is represented by the weight ratio of methylated DNA to unmethylated DNA recovered by the MeDIP method ([weight of methylated DNA]/[weight of unmethylated DNA]).

The present hybridoma is obtained by fusing antibody-producing cells obtained from an animal immunized with an antigen containing 5-methyl-dCpdGp with myeloma cells.

Preparation of the present hybridomas, production of monoclonal antibodies from the hybridomas and the method for immunoprecipitation of methylated DNA using the antibodies are described hereinafter.

These methods per se are well-known techniques to a person skilled in the art. For example, the method for preparation of hybridomas is described in Hybridoma Techniques, Cold Spring Harbor Laboratory, 1980; and *Saibo Soshiki Kagaku* (Histocytochemistry), Shuji Yamashita et al., Ed. Japan Society of Histochemistry and Cytochemistry, Gakusai Kikaku, 1986, and the method for immunoprecipation of methylated DNA is described in *Epigenetics Jikken Protocol* (Epigenetics Experimental Protocols), Toshikazu Ushijima, Yoichi Magai et al., Yodosha, 2008.

1. Preparation of Present Hybridomas

The present hybridomas may be prepared as follows. Generally, the method of preparing hybridomas may comprise the following steps:

(1) preparing an antigen for immunization;
(2) immunizing an animal with the antigen;
(3) isolating antibody-producing cells from the animal;
(4) preparing myeloma cells to be used in fusion with antibody-producing cells;
(5) fusing antibody-producing cells with myeloma cells to obtain hybridomas;
(6) selection-culturing hybridomas;
(7) screening a hybridoma producing a desired antibody; and
(8) cloning the hybridoma selected in the screening.

These steps are now described in detail.

(1) Preparation of Antigen

In order to prepare the present hybridomas, the antigen containing 5-methyl-dCpdGp is used as the antigen for immunization.

The antigen containing 5-methyl-dCpdGp may be an antigen containing a conjugate of a compound containing at least 5-methyl-dCpdGp as a hapten and an appropriate carrier molecule which can impart immunogenicity to the compound in immunological procedures. The antigen may further contain an auxiliary agent such as an adjuvant.

The compound containing 5-methyl-dCpdGp is preferably a nucleic acid containing 5-methyl-dCpdGp and more preferably DNA containing 5-methyl-dCpdGp.

The antigen for immunization used for preparation of the present hybridomas is preferably prepared by dissolving or suspending the conjugate of 5-methyl-dCpdGp with the carrier molecule in an appropriate buffer (e.g. phosphate buffer) and adding an auxiliary agent such as Freund's complete or incomplete adjuvant or alum.

The carrier molecule may be a molecule which is usually used in immunological procedures and can cause immunogenicity when it binds to a hapten, and includes Bovine Serum Albumin (BSA), Ovalbumin (OVA), and Keyhole Limpet Hemocyanin (KLH). Among these, KLH is preferred.

The conjugate of the hapten and the carrier molecule may include a conjugate containing an amide bond between a carboxylic group and an α-amino group and a conjugate obtained by cross-linking these substances with a cross-linking agent. The conjugate may be obtained by carbodiimide method, glutaraldehyde method, diazo condensation method, maleimidobenzoyloxy succinimide (MBS) method and the like, among which MBS method is preferred.

When MBS method is used, a phosphate group of a guanosine of 5-methyl-dCpdGp may be preliminarily bound to a linker containing a mercapto group (e.g. a $C_1$-$C_5$ alkylthiol), thereby allowing cross-linking of the mercapto group of the linker with the amino group of KLH by MBS.

(2) Immunization of Animal with Antigen

The above-mentioned antigen may be used for immunization of an animal selected from mammals and birds. The animal may be any animal which is usually used in immunological procedures. Mammals may include, for example, mouse, rat, guinea pig, rabbit, bovine, horse, goat, sheep, pig, dog, cat and the like, and birds may include, for example, chicken, duck, turkey, ostrich and the like. Among these, mouse is preferred.

The antigen may be administered to the animal by any route of subcutaneous injection, intraperitoneal injection, intravenous injection, intradermal injection or intramuscular injection. Among these, subcutaneous or intramuscular injection is preferred. Immunization may be carried out once, or more than once with an appropriate interval(s) such as 1 to 5 weeks. The amount of the antigen per immunization may be varied depending on the animal to be immunized and is preferably 1 to 1000 μg per animal.

In order to verify whether or not the antibody directed against the antigen has been produced in the immunized animal, reactivity in serum isolated from blood obtained from the animal with the antigen may be evaluated by ELISA and the like. When the reactivity is insufficient, booster immunization may be carried out.

(3) Isolation of Antibody-Producing Cells

Antibody-producing cells which may produce a desired antibody are isolated from the cells of the immunized animal. Antibody-producing cells may be the cells having antibody producing ability obtained from spleen, thymus, lymph node, peripheral blood or combination thereof, among which spleen cells or lymph node B-cells are preferred. For example, spleen cells may be isolated from the spleen of the animal after final immunization which has been verified for antibody production.

(4) Preparation of Myeloma Cells

Myeloma cells to be used for preparation of the present hybridomas may be appropriately selected from the cells generally used for preparation of hybridomas. Such myeloma cells include, for example, mouse-derived P3U1, X63.653, Sp2/0, X63-Ag8, NS-1, MPC-11 and the like and rat-derived AG1, AG2, AG3, RCY3, 210 and the like. It is preferable that antibody-producing cells and myeloma cells are derived from the same animal species.

A culture medium for myeloma cells may be selected from the media usually used for cell culture including, for example, Dulbecco's Modified Eagle medium (DMEM), Iscove's Modified Dulbecco's medium (IMDM), RPMI-1640 and the like to which fetal calf serum (FCS) is added in an appropriate amount.

(5) Cell Fusion of Antibody-Producing Cells and Myeloma Cells

Cell fusion may be carried out according to a method using Sendai virus, a method using polyethylene glycol (PEG method), a method by electric treatment (electrofusion) and the like. The PEG method can be carried out according to the method of Kohler and Milstein (Nature, 256: 495-497, 1975) in which antibody-producing cells and myeloma cells are mixed for 1 to 10 minutes at a temperature of 30 to 40° C. using 30 to 50% polyethylene glycol (average molecular weight: 1000 to 4000).

The electrofusion may be carried out by applying alternating voltage of 10 to 80V for 1 to 20 seconds to a mixed solution of antibody-producing cells and myeloma cells and then applying high voltage direct current pulse of 1 to 5 kV/cm with a pulse width of 10 to 100 μsec.

(6) Selection Culture of Hybridomas

Hybridomas obtained by cell fusion can be selected by culture on a selection medium on which only hybridomas can grow. Such selection medium is preferably a medium containing HAT (hypoxanthine, aminopterin and thymidine) or Haz (hypoxanthine-azaserine).

Selection culture of hybridomas with the HAT-containing medium is effective when a HGPRT (hypoxanthine guanine phosphoribosyl transferase) defective strain is used as a myeloma cell. Namely, hybridomas can be selectively cultured on the HAT-containing medium from the cell population after the cell fusion step, because the growth of HGPRT defective myeloma cells which did not fuse with antibody-producing cells is inhibited by HAT.

(7) Screening of Hybridomas

Screening is carried out in order to select the hybridomas capable of producing a desired antibody among the hybridomas thus cultured.

As antibodies produced by hybridomas are secreted from the cells, a culture supernatant of the hybridoma which has been grown on a selection medium is collected, and the present monoclonal antibody in the supernatant is evaluated for its presence or absence or, when present, its titer by MeDIP and ELISA methods to screen hybridomas.

(8) Cloning of Hybridomas

After obtaining hybridomas by the above screening which produce the desired monoclonal antibody, the hybridomas are cloned. Methods for cloning may include, for example, a method in which hybridomas are diluted so as to seed one cell per well (limiting dilution method), a method in which cells are seeded on a soft agarose medium before obtaining colonies, a method in which one cell is picked up by a micromanipulator, a FACS method in which one cell is separated with a cell sorter, among which the limiting dilution method is preferred because it is convenient.

Cloned hybridomas may be further subjected to repeated screening and cloning in order to select hybridomas having superior antibody titer.

The present inventors obtained, according to the above steps, clones SCR1 to SCR7 which showed preferable titer in the MeDIP method and competitive inhibition test (ELISA method) from hybridoma clones obtained by cell fusion of spleen cells from mice immunized with an antigen containing 5-methyl-dCpdGp with myeloma cells P3U1 by electrofusion.

The following Table 1 shows accession numbers and date of deposition of the clones deposited at the National Institute of Technology and Evaluation (2-5-8, Kazusa Kamatari, Kisarazu, Chiba, 292-0818, Japan).

TABLE 1

| Clones | Accession No. | Deposition date |
|--------|---------------|-----------------|
| SCR1 | NITE BP-810 | Sep. 10, 2009 |
| SCR2 | NITE BP-805 | Aug. 25, 2009 |
| SCR3 | NITE BP-811 | Sep. 10, 2009 |
| SCR6 | NITE BP-812 | Sep. 10, 2009 |

2. Preparation of Present Monoclonal Antibodies

The present monoclonal antibodies can be obtained from culture supernatants of the present hybridomas. The present monoclonal antibodies may also be obtained from ascites fluid of animals such as nude mice in which the present hybridomas have been proliferated intraperitoneally.

The present monoclonal antibodies can also be obtained by gene recombination. Namely, from genomic DNA of the present hybridomas, heavy chain and light chain genes of the present monoclonal antibodies are identified, DNA fragments having the genes are integrated into appropriate expression vectors, the obtained vectors are introduced to the cells which do not produce Ig proteins such as myeloma cells to allow them to express the present monoclonal antibodies, thereby obtaining the present monoclonal antibodies.

The above culture supernatant and ascites fluid can be directly used for the MeDIP method and the like because they contain the present monoclonal antibodies. However, in order to improve the recovery amount and concentrating ratio of methylated DNA in the MeDIP method, it is preferred that the present monoclonal antibodies used are the ones purified from the culture supernatant or ascites fluid.

A purification method of the present monoclonal antibodies may be selected from the methods well known to those skilled in the art including, for example, dialysis, ammonium sulfate fractionation, polyethylene glycol fractionation, ethanol fractionation, affinity chromatography, ion-exchange column chromatography, high performance liquid chromatography, gel filtration, freeze drying and the like. Among these purification methods, affinity chromatography is preferred and affinity chromatography using a Protein A (or G) column is more preferred.

The thus obtained monoclonal antibodies may be determined for their subclass by a well-known method such as ELISA or by using a kit.

The present monoclonal antibodies also include functional fragments which can be obtained by fragmentation of the antibodies. Such functional fragments may be fragments which retain specific binding activity for methylated DNA. These functional fragments can be prepared by, for example, treating the purified present monoclonal antibodies with papain, pepsin, trypsin and the like.

The present monoclonal antibodies have superior binding ability and specificity for methylated DNA. Therefore, they are suitably used in the MeDIP method in which methylated DNA is recovered and concentrated.

3. Methylated DNA Immunoprecipitation Method (MeDIP) Using the Present Monoclonal Antibodies In the MeDIP method using the present monoclonal antibodies (hereinafter also referred to as "the present MeDIP method") as the anti-methylated DNA antibody, higher amount of methylated DNA can be collected and concentrated than the case where conventional anti-methylated cytosine antibodies or the like are used as the anti-methylated DNA antibody.

Thus, higher amount of methylated DNA which has been highly concentrated by the present MeDIP method can be used as a sample in methylated DNA analyses.

Therefore, the present MeDIP method is suitable for preparation of samples for methylated DNA analyses.

The present MeDIP method comprises the following three steps: (1) preparing single-stranded DNA fragments from DNA extracted from a biological sample; (2) immunoprecipitating methylated DNA from the single-stranded DNA fragments using the present monoclonal antibody; and (3) recovering the immunoprecipitated methylated DNA. The present MeDIP method preferably comprise the additional step of (4) detecting the methylated DNA, in order to confirm whether or not the methylated DNA is specifically obtained after recovering DNA.

These steps are now described in detail.

(1) Extraction of DNA from Biological Sample, Fragmentation of DNA and Denaturation into Single Strand DNA is extracted from a biological sample obtained from a subject of interest. The biological sample may be any sample containing DNA from the subject of interest without limitation and may preferably include samples containing genomic DNA such as cultured cells, clinical specimens and the like. Clinical specimens specifically include blood, serum, lymphocytes, urine, nipple discharge fluid, tissues collected during surgery or biopsy.

DNA can be extracted from the biological sample by using the method well known to those skilled in the art. DNA can be extracted, for example, by mixing the biological sample and a treatment solution containing a surfactant capable of solubilizing cells and/or tissues (sodium cholate, sodium dodecyl sulfate etc.) followed by physical treatment (stirring, homogenization etc.) for releasing DNA contained in the biological sample into a solution.

The obtained DNA may be purified, for example, by collecting a supernatant after centrifugation of the above solution and subjecting the supernatant to phenol/chloroform extraction. Extraction and purification of DNA from the biological sample can be carried out with commercial kits.

The obtained DNA is then fragmented to, for example, about 200 to 1000 bp.

Fragmentation of DNA can be carried out by ultrasonication, alkaline treatment, enzyme treatment and the like. When alkaline treatment is carried out with sodium hydroxide, for example, a sodium hydroxide solution can be added to the DNA solution to a final concentration of 0.1 to 1.0N and the mixture is incubated at 10 to 40° C. for 5 to 15 minutes, thereby fragmenting the DNA. Restriction enzymes may be used for enzyme treatment. The restriction enzyme may be appropriately selected according to base sequences of DNA, which may include MseI, BamHI and the like.

The thus obtained DNA fragments are heated for denaturation before quenching the fragments to obtain single strands. For example, single-stranded DNA fragments can be obtained by heating the solution containing DNA fragments at 94 to 96° C. for 5 to 15 minutes followed by quenching the solution to 2 to 4° C.

Because the present monoclonal antibodies are added to the solution containing single-stranded DNA fragments thus obtained in the following step of immunoprecipitation, the solution is preferably diluted with a buffer generally used in immunoprecipitation. An appropriate amount of an antibody-binding carrier may be added to the diluted solution before rotation to remove proteins which non-specifically bind to the carrier (this treatment is hereinafter referred to "pre-clear treatment"). The antibody-binding carrier may be any carrier capable of specifically binding to the Fc region of IgG including, for example, Protein A (or G) Sepharose beads.

(2) Immunoprecipitation of Methylated DNA

Methylated DNA is immunoprecipitated by adding to the solution containing single-stranded DNA fragments an appropriate amount of the present monoclonal antibody, bringing them into contact for 20 minutes to 24 hours to allow reaction therebetween and adding the antibody-binding carrier in order to contact them for further 20 minutes to 3 hours.

An added amount (final concentration) of the present monoclonal antibody is selected from the range of 0.01 to 100 µg/ml to the solution containing single-stranded DNA fragments (1 µg/ml). Immunoprecipitation of methylated DNA using the present monoclonal antibody can be carried out at an ambient temperature of 4 to 50° C. and preferably in the range of 4 to 37° C.

Immunoprecipitation of methylated DNA may be carried out by adding a complex of the antibody-binding carrier with the present monoclonal antibody prepared beforehand to the solution containing single-stranded DNA fragments.

(3) Recovery of Methylated DNA

The antibody-binding carrier is recovered by centrifugation and the like and is then washed with a suitable washing buffer for several times, and methylated DNA captured by the present monoclonal antibodies attached to the antibody-binding carrier is eluted by using an appropriate elution buffer.

The obtained methylated DNA may be purified by methods well known to those skilled in the art such as phenol/chloroform method, ethanol precipitation and the like or by using a kit.

(4) Detection of Methylated DNA

Specific recovery of the methylated DNA by immunoprecipitation can be verified by well-known methylated DNA detection methods such as PCR, quantitative PCR, bisulfite sequencing and the like.

(i) Detection by PCR or Quantitative PCR

Detection of methylated DNA by PCR or quantitative PCR may be carried out with conventionally available kits for PCR or quantitative PCR. Methylated DNA can be detected in PCR by confirming the presence of amplified products in agarose electrophoresis.

Amplification reaction conditions may be appropriately determined by those skilled in the art depending on a base sequence of a region to be amplified, the length of the base sequence to be amplified and the like.

Amplification primers may be primers for a sequence of a methylated gene (for detection) and primers for a sequence of an unmethylated gene (for negative control) in the biological sample such as cells and tissues.

(ii) Detection by Bisulfite Sequencing

DNA recovered by the MeDIP method is subjected to bisulfite treatment in order to detect methylated DNA by bisulfite sequencing.

In bisulfite treatment, a solution of bisulfites such as sodium, potassium, calcium or magnesium bisulfite is added to the DNA solution to convert an unmethylated cytosine (C) in the DNA to uracil (U) by deamination reaction. On the other hand, bisulfites do not act on a methylated cytosine, so that the above base conversion does not occur. Thus, if DNAs are different in their methylation status, this difference is converted to a difference in base sequences (C or U) by bisulfite treatment.

Methylation of DNA can be detected by converting an unmethylated cytosine in DNA to uracil by bisulfite treatment and sequencing the DNA to detect any difference from the original base sequence.

The present invention is now described in detail by means of examples, which do not limit the present invention.

EXAMPLES

Example 1

Preparation of Hybridomas

1. Preparation of Antigen for Immunization and Antigen for Screening by ELISA

An antigen for immunization was prepared by cross-linking 5'-(5-methyl-2'-deoxycytidine-3'-phospho)-2'-deoxyguanosine 3'-phosphate 3-mercaptopropyl ester (hereinafter also referred to as "5-methyl-dCpdGpC3H6SH"), as shown in the following formula (II), which is a binding product of 5-methyl-dCpdGp and propane thiol with a linker therebetween, with KLH as a carrier by MBS method.

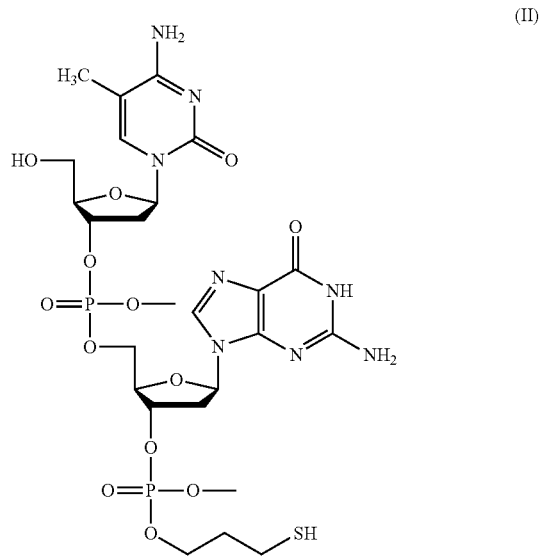

(II)

An antigen for screening by ELISA was prepared by cross-linking 5-methyl-dCpdGpC3H6SH with BSA by MBS method.

The antigen for immunization (100 μg) was mixed with 100 μl Freund's complete adjuvant (FCA) for emulsification to prepare a FCA-antibody solution. The antigen for immunization (100 μg) was mixed with 100 μl Freund's incomplete adjuvant (FIA) for emulsification to prepare a FIA-antigen solution.

2. Immunization of Mice

Female Balb/c mice (9-week old; Charles River Laboratories Japan Inc.) were intraperitoneally administered with 100 μl of the FCA-antigen solution (primary immunization). The mice were then intraperitoneally administered with 100 μl of the FIA-antigen solution once every 2 weeks for 6 times (booster immunization).

3. Cell Fusion of Spleen Cells and Myeloma Cells

After 14 days of the final booster immunization, spleen of mice was aseptically collected. Lipid was removed from spleen in the RPMI-1640 medium. The medium was injected to spleen after removal of lipid with a syringe, both ends of the spleen were trimmed off with forceps and cells were recovered from spleen into the medium. The obtained cells were dispersed in the medium and passed through a stainless mesh to obtain a suspension of spleen cells.

The obtained spleen cells ($1 \times 10^8$ cells) and murine myeloma cells P3U1 ($2 \times 10^7$ cells) were mixed and fused with an electrofusion apparatus SSH-2 (Shimadzu Corporation). The cell fusion was carried out by applying alternating voltage (40V) for 10 seconds to the mixed solution of spleen cells and myeloma cells and then applying direct current pulse (2.3 kV/cm, pulse width 40 μsec).

4. Hybridoma Culture

Hybridomas were suspended at $1.2 \times 10^6$ cells/ml in a HAT-containing medium (RPMI-1640 medium containing $1 \times 10^{-4}$ M hypoxanthine, $4 \times 10^{-7}$ M aminopterine, $1.5 \times 10^{-5}$ M thymidine and 20% FCS) and seeded into wells of a 96-well plate (Nunc; hereinafter referred to as the culture plate) at $1.2 \times 10^5$ cells/well. The culture plate was placed in an incubator at 37° C. and 5% $CO_2$ to initiate hybridoma culture. After 10 days of culturing, colonies of hybridomas appeared and were screened for monoclonal antibody production.

5. Screening of Hybridomas by ELISA

To a phosphate buffer (140 mM NaCl, 2.7 mM KCl, 10 mM $Na_2HPO_4$ and 1.8 mM $KH_2PO_4$ (pH 7.4); hereinafter referred to as PBS) was added the antigen for screening prepared in the above 1. at a final concentration of 5 µg/ml to prepare a immobilization antigen solution. The immobilization antigen solution (50 µl) was added to wells of the 96-well polystyrene microtiter plate (hereinafter referred to as the antigen immobilized plate). The antigen immobilized plate was left overnight at 4° C. and the wells were then washed with PBS (200 µl/well). Following washing, Block Ace (Dainippon Pharmaceutical) was added to the wells of the antigen immobilized plate at 200 µl/well, which was then left at room temperature for an hour. The wells were then washed with PBS containing 0.05% Tween20 (hereinafter also referred to as "PBS-T"; 200 µl/well).

The culture supernatant of hybridomas was obtained from the wells of the culture plate, distributed to the wells of the antigen immobilized plate at 50 µl per well and stirred at room temperature for an hour. After stirring, the wells were washed twice with PBS-T (200 µl/well). After washing, a horse radish peroxidase (HRP)-labeled anti-mouse Ig polyclonal antibody (Cappel) was added to the wells of the antigen immobilized plate at 100 µl per well and left for reaction at room temperature for an hour. After the reaction, the wells were washed twice with PBS-T (200 µl/well). After washing, 100 µl of a substrate solution containing a substrate for HRP, orthophenylene diamine (OPDA) (10 mg/25 ml OPDA+2 µl 30% $H_2O_2$/25 ml citric acid solution) was added to each well, and the antigen immobilized plate was left in the dark at room temperature for 20 minutes. A reaction termination solution containing 2N $H_2SO_4$ was added at 100 µl per well prior to measure the absorbance at 490 nm for the reaction solution in the wells with a microplate reader (Model 3550: Bio-Rad).

6. Screening of Hybridomas by MeDIP Method

Genomic DNA (4 µg) extracted from human breast cancer cell strain MCF7 was subjected to an overnight reaction with a restriction enzyme MseI (NEB) at 37° C. in order to fragment DNA in to 300 to 1000 bp. The DNA fragments after reaction were denatured at 95° C. for 10 minutes and quenched at 4° C. to obtain single-stranded DNA fragments. The obtained single-stranded DNA fragments were diluted in a dilution buffer provided with Chromatin Immunoprecipitation assay kit (Upstate Biotechnology) with following an accompanying instruction. Protein G Sepharose beads (GE Healthcare) were added followed by rotation at 4° C. for 30 minutes to carry out pre-clear treatment. The supernatant collected after centrifugation was dispensed in tubes to obtain MeDIP samples and control samples.

The MeDIP sample and control sample were added with a culture supernatant of a hybridoma which showed high absorbance in the above screening by ELISA and with a normal murine anti-IgG antibody (SantaCruz), respectively. They were reacted at 4° C. for overnight under rotation, added with Protein G Sepharose beads (GE Healthcare) and rotated at 4° C. for additional one hour for immunoprecipitation. Due to this, the complex of the antibody contained in the culture supernatant and DNA was bound to Protein G Sepharose beads, which were then collected. The collected beads were washed with a wash buffer in Chromatin Immunoprecipitation assay kit (Upstate) and then DNA in the complex was eluted with an elution buffer in the kit. The eluted DNA was subjected to the reaction with proteinase K and purified with Qiaquick PCR purification kit (QIAGEN).

The above washing, elution and purification were carried out by following the instructions of the kits.

In order to confirm whether or not methylated DNA was specifically recovered in the MeDIP method, PCR and agarose electrophoresis were carried out.

(i) Preparation of PCR Reactions

The reaction solution (25 µl) was prepared by mixing the following reagents:

| | |
|---|---|
| 2 x FastStart Universal SYBR Green Master (Rox) (ROCHE) | 12.5 µl |
| Forward (F) primer (10 µM) | 1 µl |
| Reverse (R) primer (10 µM) | 1 µl |
| Recovered DNA | 1 µl |
| $dH_2O$ | 9.5 µl |

Sequences of the primers used are shown below.

As a primer set for methylated DNA detection, a primer set was used for amplification of the promoter region of GSTP1 gene which is known to be methylated in MCF7 cells. GSTP1 primer sequences are shown below.

```
F: 5'-GAGGCCTTCGCTGGAGTT-3'      (SEQ ID NO: 1)

R: 5'-GTACTCACTGGTGGCGAAGA-3'    (SEQ ID NO: 2)
```

As a primer set for unmethylated DNA detection, a primer set was used for amplification of a region which exists in human chromosome 14 and is not methylated because of absence of a CpG sequence (hereinafter referred to as the CGF-1 region). The sequence of the CGF-1 region is shown below.

<CGF-1 Region>

```
                                             (SEQ ID NO: 10)
GGAGGAGTCA AGAGAAGTTG GAAGCCAACT GAGAGAGAGG

GAAGGCTTGA AGTGGTCAGG ACAGTGAACA CCTAAGAGAC

ATCCACTGAA TTTGCCCACT AGGAAGCCAT TAGTGACTTC

AATAGGAACA TCTTCAGTGC ATCATGAAGG CCAAAGATTG

CCATGAAAGA GAGGAATGGA AATGGAGTGT GGG
```

The sequences of the CGF-1 primers are shown below.

```
F: 5'-GGAGGAGTCAAGAGAAGTTGAAGC-3'   (SEQ ID NO: 3)

R: 5'-CCCACACTCCATTTCCATTCCTC-3'    (SEQ ID NO: 4)
```

(ii) PCR Reaction Conditions

PCR was carried out with the above reaction solution under the following conditions.

One cycle of 95° C. for 10 minutes;

45 cycles of 95° C. for 30 seconds, 66° C. for 15 seconds and 72° C. for 30 seconds; and one cycle of 95° C. for 1 minute, 66° C. for 30 seconds and 95° C. for 30 seconds.

(iii) Agarose Gel Electrophoresis

The PCR products were migrated in a 2% agarose gel by electrophoresis to verify the amplified products. Hybridomas in the supernatants were selected which contained higher amount of the amplified products of GSTP1 gene and less amount of the amplified amount of CGF-1 region.

7. Cloning of Hybridomas

The selected hybridomas were cloned by limiting dilution using Hybridoma Cloning Factor (IGEN). At 10 days after cloning, hybridomas producing antigens (antigen-producing hybridomas) were cloned in the same manner as the above screening of hybridomas using ELISA.

8. Selection of Antibody-Producing Hybridomas by Competitive Inhibition Test

The solutions of the following compounds 1 and 2 (1 mM) were respectively prepared, heated at 95° C. for 10 minutes and then cooled on ice for 2 minutes.
Compound 1: 5-methyl-dCpdGpC3H6SH
Compound 2: NNNCGNNN (wherein "N" represents any nucleotide)

An immobilization antigen solution was prepared by adding to PBS the antigen for screening to the final concentration of 5 µg/ml. The immobilization antigen solution (50 µl) was added to the wells of a 96-well polystyrene microtiter plate (hereinafter referred to as the antigen immobilized plate). The antigen immobilized plate was left overnight at 4° C. and the wells were washed with PBS (200 µl/well). Following washing, Block Ace (Dainippon Pharmaceutical) was added to the wells of the antigen immobilized plate at 200 µl/well, which was then left at room temperature for an hour. The wells were then washed with PBS-T (200 µl/well).

The culture supernatant of hybridomas and the solution of the compound 1 (50 µl each) were then respectively added to the wells of the antigen immobilized plate, which was then stirred at room temperature for an hour. After stirring, the wells were washed twice with PBS-T (200 µl/well). After washing, the HRP-labeled anti-mouse Ig polyclonal antibody (Cappel) was added at 100 µl per well and left for reaction at room temperature for an hour. After the reaction, the wells were washed twice with PBS-T (200 µl/well). After washing, 100 µl of the above substrate solution containing OPDA was added to each well, and the antigen immobilized plate was left in the dark at room temperature for 20 minutes. A reaction termination solution containing 2N $H_2SO_4$ was added at 100 µl per well prior to measure the absorbance at 490 nm for the reaction solution in the wells with a microplate reader (Model 3550: Bio-Rad).

Accordingly, cross-reaction of the antibodies produced by the antibody-producing hybridomas to the compound 1 was examined. Similarly, when the solution of the compound 1 was replaced with the solution of the compound 2, cross-reaction of the antibodies produced by the antibody-producing hybridomas to the compound 2 was also examined. Based on these results, antibody-producing hybridomas were selected which cross-reacted with the compound 1 but not to the compound 2.

The hybridomas selected by repeating the cloning and competitive inhibition test twice were screened by the above MeDIP method for hybridoma screening to obtain seven hybridoma clones (SCR1 to SCR7).

As shown in Table 1, SCR2 was deposited on Aug. 25, 2009 under the accession number of NITE BP-805 and SCR1, SCR3 and SCR6 were deposited on Sep. 10, 2009 under the accession numbers of NITE BP-810, NITE BP-811 and NITE BP-812, respectively at the National Institute of Technology and Evaluation (2-5-8, Kazusa Kamatari, Kisarazu, Chiba, 292-0818, Japan).

Example 2

Evaluation of Monoclonal Antibody Titer by MeDIP Method

1. Recovery of Methylated DNA by MeDIP Method

With the similar procedures as Example 1, 6., genomic DNA (4 µg) extracted from MCF7 was used for preparation of a diluted solution of single-stranded DNA fragments, which was then subjected to the pre-clear treatment to give MeDIP samples and control samples.

The culture supernatants of SCR1 to SCR7, commercially available anti-methylated cytosine antibodies and anti-methylated cytidine antibodies were respectively added to the MeDIP samples, and a culture supernatant (negative control supernatant) of the hybridoma whose antibody-producing capacity was not confirmed in the screening using a normal murine anti-IgG antibody (SantaCruz), a normal rabbit anti-IgG antibody (SantaCruz) and the above ELISA was added to the control sample. These were rotated overnight at 4° C. for reaction between the antibody and the antigen before addition of Protein G Sepharose beads (GE Healthcare) and immunoprecipitation by rotation at 4° C. for an hour. DNA was eluted from the beads and purified in the same manner as described in Example 1, 6.

Table 2 below shows the commercially available antibodies used with their manufacturers and clone names.

TABLE 2

| Manufacturer | Antibody name | Clone name | immunized animal |
|---|---|---|---|
| Calbiochem | Anti-5-Methylcytosine Mouse mAb | 162 33D3 | Mouse |
| abcam | 5-Methylcytidine | 33D3 | Mouse |
| Eurogentec | 5-Methylcytidine | monoclonal | Mouse |
| Aviva System Biology | 5-Methylcytosine | 33D3 | Mouse |
| Novus Biologicals | Cytosine (5-Methyl) | polyclonal | Sheep |
| Diagenode | 5-methyl cytidine | monoclonal | Mouse |

2. Quantitative PCR

In order to evaluate the recovery amount and concentrating ratio of methylated DNA by the MeDIP method, quantitative PCR was carried out.
(i) Preparation of PCR reactions The reaction solution (25 µl) was prepared by mixing the following reagents. Reaction solutions were also prepared for the serial dilutions of genomic DNA extracted from MCF7 (0.1, 1.0, 10 and 100 ng/µl) to prepare samples for calibration curve.

| | |
|---|---|
| 2 x FastStart Universal SYBR Green Master (Rox) (ROCHE) | 12.5 µl |
| F primer (10 µM) | 1 µl |
| R primer (10 µM) | 1 µl |
| Recovered DNA | 1 µl |
| $dH_2O$ | 9.5 µl |

The primers used were the above GSTP1 primers (SEQ ID NOs: 1 and 2) and CGF-1 primers (SEQ ID NOs: 3 and 4).

Quantitative PCR was carried out for the above reaction solutions with Mx3005P (Stratagene) under the following reaction conditions.
(ii) Reaction Conditions of Quantitative PCR One cycle of 95° C. for 10 minutes;
45 cycles of 95° C. for 30 seconds, 66° C. for 15 seconds and 72° C. for 30 seconds; and
one cycle of 95° C. for 1 minute, 66° C. for 30 seconds and 95° C. for 30 seconds.

3. Results

Figure 2:
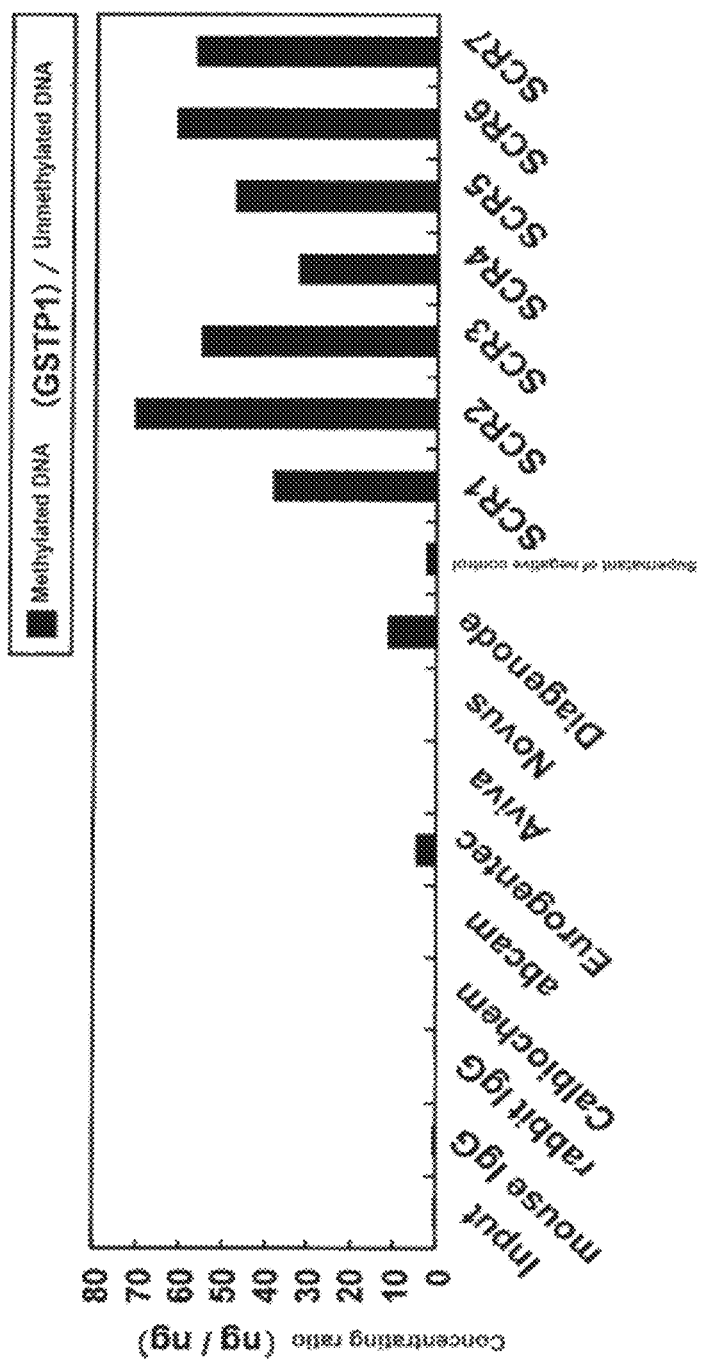
FIG. 2 is a bar graph showing the concentrating ratios of methylated DNA recovered by the MeDIP method using the culture supernatants of the present hybridomas and various commercial antibodies.

FIGS. 1 and 2 show the recovery amounts and concentrating ratios of methylated DNA obtained by the MeDIP method using the respective antibodies. FIG. 1 is a bar graph showing the amounts of methylated DNA and unmethylated DNA recovered by the MeDIP method using the culture supernatants of hybridomas SCR1 to SCR7 and various commercial antibodies. FIG. 2 is a bar graph showing the concentrating ratios of methylated DNA recovered by the MeDIP method using the culture supernatants of hybridomas SCR1 to SCR7 and various commercial antibodies.

FIGS. 1 and 2 show that the recovery amount and concentrating ratio of methylated DNA by the culture supernatants of SCR1 to SCR7 are significantly higher than those obtained with commercial antibodies.

For example, FIG. 1 shows that the culture supernatants of SCR1 to SCR7 gave significantly higher recovery amounts of methylated DNA by the MeDIP method than various commercial antibodies. More specifically, the recovery amounts were 45.9 times higher for SCR1, 136.4 times higher for SCR2, 109.3 times higher for SCR3, 54 times higher for SCR4, 56.6 times higher for SCR5, 78.1 times higher for SCR6 and 132.8 times higher for SCR7 than the antibody from Novus which showed the highest recovery amount among commercial antibodies. These results suggest that the antibodies produced by the present hybridomas may have higher binding ability for methylated DNA than various commercial antibodies.

It was also found that when the culture supernatants of SCR1 to SCR7 were used in the MeDIP method, the recovery amounts of unmethylated DNA did not increase in contrast to the increased amount of methylated DNA. It suggests that the antibodies produced by the present hybridomas have higher specificity for methylated DNA than various commercial antibodies.

FIG. 2 shows that the culture supernatants of SCR1 to SCR7 gave higher concentrating ratios of methylated DNA in the MeDIP method than various commercial antibodies. More specifically, the concentrating ratios were 67 times higher for SCR1, 124 times higher for SCR2, 97 times higher for SCR3, 57 times higher for SCR4, 84 times higher for SCR5, 108 times higher for SCR6 and 99 times higher for SCR7 than Input.

The concentrating ratios were 3.3 times higher for SCR1, 6.1 times higher for SCR2, 4.8 times higher for SCR3, 2.8 times higher for SCR4, 4.1 times higher for SCR5, 5.3 times higher for SCR6 and 4.9 times higher for SCR7 than the antibody from Diagenode which showed the highest concentrating ratio among commercial antibodies.

These results show that the antibodies produced by the present hybridomas have higher specificity for methylated DNA than various commercial antibodies.

Example 3

Purification of Monoclonal Antibody from Ascites Fluid

1. Preparation of Ascites Fluid

Five Balb/c nude mice (6-week old, female: Charles River Laboratories Japan Inc.) were intraperitoneally inoculated with the hybridoma SCR2 ($1 \times 10^7$ cells/mouse). One week after the inoculation, mice were booster inoculated with SCR2 ($1 \times 10^7$ cells/mouse). Two weeks after the booster inoculation, ascites fluid was collected from the mice using a syringe.

2. Ammonium Sulfate Precipitation

To 17.5 ml of the obtained ascites fluid was gradually added ammonium sulfate at the amount of 50% saturation (5.1 g) and the precipitation was obtained after cooling and stirring. The precipitation was collected and dissolved in PBS to obtain the solution, which was then dialyzed in a dialysis tube against 4 L PBS for 12 days. After dialysis, the solution in the tube was filtered with a 0.45-µm filter to obtain the purified monoclonal antibody (279 mg).

Sub-class of the obtained monoclonal antibody was evaluated with Mouse monoclonal antibody isotyping test kit (Serotec), which was found to be IgG2a (κ).

The thus obtained monoclonal antibody from SCR2 was used in the following Example 4.

Example 4

Characterization of Temperature Property of Monoclonal Antibody

1. MeDIP method

With the similar procedures as Example 1, 6., genomic DNA (4 µg) extracted from MCF7 was used for preparation of a diluted solution of single-stranded DNA fragments, which was then subjected to the pre-clear treatment to give MeDIP samples and control samples.

The monoclonal antibody from SCR2 and the anti-methylated cytidine antibody from Diagenode were respectively added to the MeDIP samples, and a normal murine anti-IgG antibody (SantaCruz) was added to the control sample. These were rotated overnight at 4° C., for an hour at 4° C., for an hour at a room temperature and for an hour at 37° C. for reaction between the antibody and the antigen before addition of Protein G Sepharose beads (GE Healthcare) and immunoprecipitation by rotation at each temperature for an hour. DNA was eluted from the beads and purified in the same manner as described in Example 1, 6.

2. Quantitative PCR

In order to evaluate the recovery amount and concentrating ratio of methylated DNA by the MeDIP method, quantitative PCR was carried out.

(i) Preparation of PCR Reactions

The reaction solution (25 µl) was prepared by mixing the following reagents. Reaction solutions were also prepared for the serial dilutions of genomic DNA extracted from MCF7 (0.1, 1.0, 10 and 100 ng/µl) to prepare samples for calibration curve.

| | |
|---|---|
| 2 x FastStart Universal SYBR Green Master (Rox) (ROCHE) | 12.5 µl |
| F primer (10 µM) | 1 µl |
| R primer (10 µM) | 1 µl |
| Recovered DNA | 1 µl |
| dH$_2$O | 9.5 µl |

The primer sets for methylated DNA detection were the primer sets for amplification of FBRS gene and REXO1L1 gene. The present inventors have confirmed that the regions amplified with these primer sets are methylated in MCF7 cells (see Reference Example below).

The primers for unmethylated DNA detection were the CGF-1 primer set.

The sequences of the FBRS primer set and REXO1L1 primer set are shown below:

<FBRS Primer Set>

```
                                        (SEQ ID NO: 5)
F: 5'-GAGAAGTAGTTGGAAGGAGAGG-3';
and
                                        (SEQ ID NO: 6)
R: 5'-CCCTACACTAACTACAATAATTTAATATCC-3'
```

<REXO1L1 Primer Set>

```
                                        (SEQ ID NO: 7)
F: 5'-GTAGGATGGTTTGGATTTGGGGTAA-3';
and
                                        (SEQ ID NO: 8)
R: 5'-CAACTACTCCTAACTCTATAAACTACCAA-3'
```

Quantitative PCR was carried out for the above reaction solutions with Mx3005P (Stratagene) under the following reaction conditions.

(ii) Reaction Conditions of Quantitative PCR

One cycle of 95° C. for 10 minutes;

45 cycles of 95° C. for 30 seconds, 66° C. for 15 seconds and 72° C. for 30 seconds; and one cycle of 95° C. for 1 minute, 66° C. for 30 seconds and 95° C. for 30 seconds.

Quantitative PCR for the reaction solutions containing the FBRS primer set was carried out under the following conditions.

One cycle of 95° C. for 10 minutes;

45 cycles of 95° C. for 30 seconds, 63° C. for 15 seconds and 72° C. for 30 seconds; and one cycle of 95° C. for 1 minute, 63° C. for 30 seconds and 95° C. for 30 seconds.

3. Results

Figure 3:
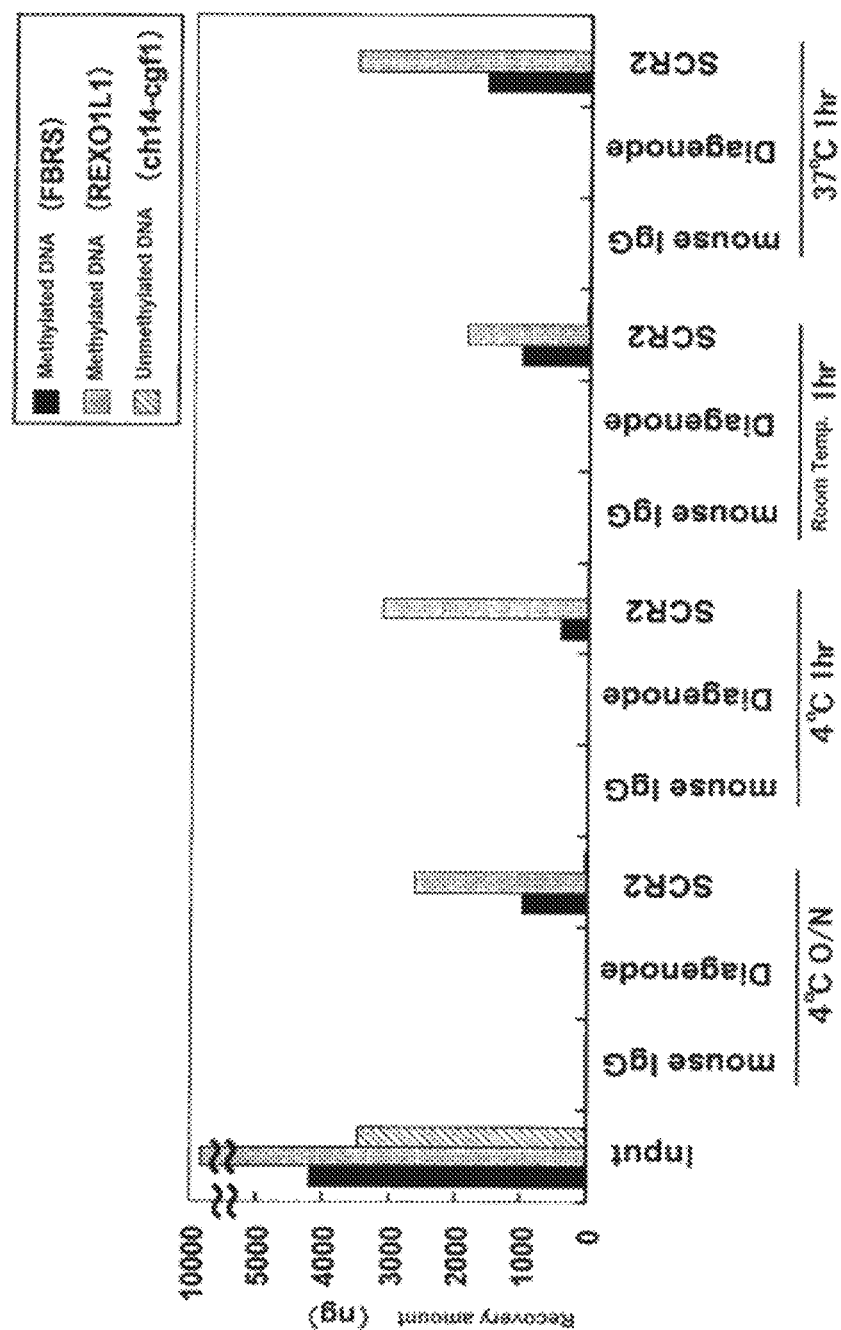
FIG. 3 is a bar graph showing the amounts of methylated DNA and unmethylated DNA recovered by the MeDIP method using the present monoclonal antibody or the commercial antibody under various conditions.
Figure 4:
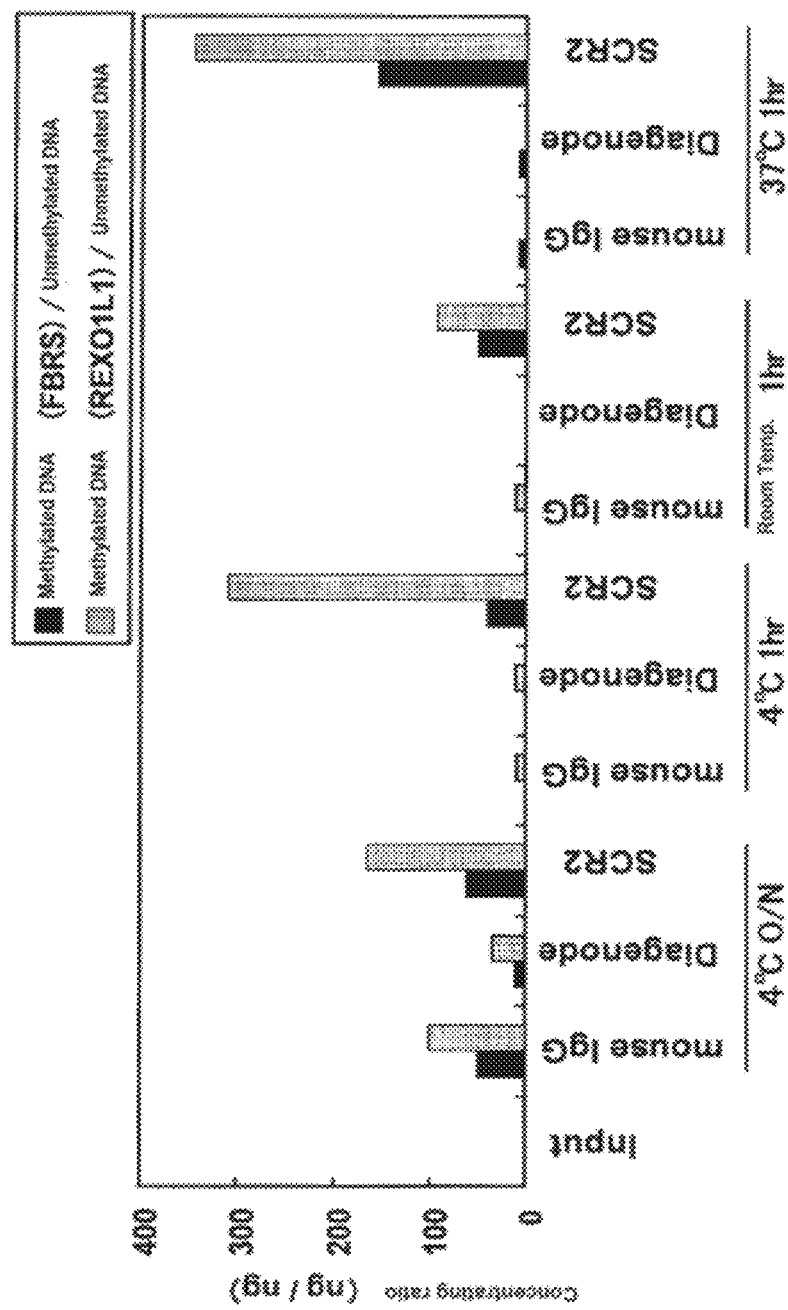
FIG. 4 is a bar graph showing the concentrating ratios of methylated DNA recovered by the MeDIP method using the present monoclonal antibody or the commercial antibody under various conditions.

FIGS. 3 and 4 show the recovery amounts and concentrating ratios of methylated DNA obtained by the MeDIP method under various conditions. FIG. 3 is a bar graph showing the amounts of methylated DNA and unmethylated DNA recovered by the MeDIP method using the monoclonal antibody from SCR2 or the commercial antibody under various conditions. FIG. 4 is a bar graph showing the concentrating ratios of methylated DNA recovered by the MeDIP method using the monoclonal antibody from SCR2 or the commercial antibody under various conditions.

FIG. 3 shows that the monoclonal antibody from SCR2 gave high recovery amounts of methylated DNA in the MeDIP method under respective reaction conditions. It is also shown that the monoclonal antibody from SCR2 gave almost no increase in the recovery amount of unmethylated DNA in the MeDIP method under any reaction conditions. It is thus suggested that the monoclonal antibody obtained from SCR2 has high binding ability and specificity for methylated DNA under respective reaction conditions.

It is also shown in FIG. 4 that the monoclonal antibody from SCR2 gave high concentrating ratios of methylated DNA in the MeDIP method under respective reaction conditions. It is thus suggested that the monoclonal antibody obtained from SCR2 has high specificity for methylated DNA under respective reaction conditions.

The above results show that it is possible to carry out the MeDIP method under any reaction conditions of at 4° C. for one hour, at a room temperature for one hour and at 37° C. for one hour with the present monoclonal antibody, contrary to the conventional MeDIP method in which the reaction is carried out overnight at 4° C.

Reference Example

Detection of Methylated DNA by Bisulfite Sequencing

In order to confirm that the regions amplified with the primer sets for FBRS gene and REXO1L1 gene used in Example 4 were methylated in MCF7 cells, bisulfite sequencing was carried out.

1. Preparation of Bisulfite-Treated DNA Solution

Genomic DNA (2 μg) extracted from MCF7 cells was diluted in 19 μl water, to which 1 μl of a 6M sodium hydroxide aqueous solution was added to the final concentration of 0.3N and incubated at 37° C. for 15 minutes for denaturation.

To the above DNA solution was added 120 μl of a 3.6M sodium bisulfite/0.6M hydroquinone solution and then subjected to bisulfite treatment with 15 cycles of 95° C. for 30 seconds and 50° C. for 15 minutes. The treated solution was desalted with Wizard® DNA Clean-up System (Promega), and eluted with 50 μl of TE buffer to obtain the DNA solution in which an unmethylated cytosine was converted to uracil.

To the DNA solution was added 5 μl of a 3N sodium hydroxide aqueous solution and incubated at room temperature for 5 minutes before purification with Qiaquick PCR purification kit (QIAGEN) to obtain a DNA solution.

2. Sequencing

PCR was carried out using the obtained DNA solution as a template with the primer sets for FBRS gene and REXO1L1 gene.

(i) Preparation of PCR Reactions

The reaction solution (15 μl) was prepared by mixing the following reagents.

| | |
|---|---|
| 10 x Ex Taq ® buffer (TaKaRa Bio) | 12.5 μl |
| dNTP mix (2.5 mM) | 1.2 μl |
| F primer (10 μM) | 0.6 μl |
| R primer (10 μM) | 0.6 μl |
| DNA solution | 1 μl |
| Ex Taq ® polymerase (TaKaRa Bio) | 0.12 μl |
| dH$_2$O | 9.98 μl |

PCR was carried out for the above reaction solutions under the following conditions.

(ii) Reaction Conditions of Quantitative PCR

One cycle of 95° C. for 4.5 minutes;

40 cycles of 95° C. for 30 seconds, 66° C. for 15 seconds and 72° C. for 30 seconds; and left at 4° C.

Quantitative PCR for the reaction solutions containing the FBRS primer set was carried out under the following conditions.

One cycle of 95° C. for 4.5 minutes;

40 cycles of 95° C. for 30 seconds, 60° C. for 15 seconds and 72° C. for 30 seconds; and left at 4° C.

The obtained PCR products were introduced in the pCR® 2.1 vector in TA cloning kit (Invitrogen), plasmids were collected and sequenced with M13Rv primer.

The sequence of the M13Rv primer is as follows.

5'-CAGGAAACAGCTATGAC-3'    (SEQ ID NO: 9)

Table 3 shows the methylation status of CpG sequences in the amplified regions of FBRS and REXO1L1 genes based on the sequencing results. In this Table, the numbers shown in the row of "CpG sequence" correspond to the ordinal numbers of CpG sequences from the 5'-end of the amplified regions of these genes. ● represents a methylated CpG sequence and ○ represents an unmethylated CpG sequence.

TABLE 3

| | CpG sequence | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| FBRS | | | | | | | | | | | | | | |
| Clone 1 | O | ● | ● | ● | ● | ● | ● | ● | ● | ● | ● | ● | O | ● |
| Clone 2 | ● | ● | ● | ● | ● | ● | ● | ● | ● | ● | O | ● | O | ● |
| Clone 3 | ● | ● | ● | ● | O | ● | ● | ● | ● | ● | ● | ● | ● | ● |
| Clone 4 | ● | ● | ● | ● | ● | ● | ● | ● | ● | ● | O | ● | O | ● |
| Clone 5 | ● | ● | O | ● | ● | ● | ● | ● | ● | ● | ● | ● | ● | ● |
| Clone 6 | ● | ● | ● | ● | ● | ● | ● | ● | ● | ● | ● | ● | ● | ● |
| REXO1L1 | | | | | | | | | | | | | | |
| Clone 1 | ● | ● | ● | ● | ● | ● | ● | ● | O | ● | ● | ● | O | ● |
| Clone 2 | ● | ● | ● | ● | ● | ● | ● | ● | ● | ● | ● | ● | ● | ● |
| Clone 3 | ● | ● | ● | ● | ● | ● | ● | ● | ● | ● | ● | ● | ● | ● |

| | CpG sequence | | | | | | | | | | | | |
|---|---|---|---|---|---|---|---|---|---|---|---|---|---|
| | 15 | 16 | 17 | 18 | 19 | 20 | 21 | 22 | 23 | 24 | 25 | 26 | 27 |
| Clone 1 | O | ● | ● | ● | ● | ● | ● | ● | O | ● | ● | ● | ● |
| Clone 2 | ● | ● | ● | ● | ● | ● | ● | ● | O | O | O | O | O |
| Clone 3 | ● | ● | ● | ● | ● | ● | ● | ● | ● | O | O | O | O |

It was found from Table 3 that the most of the CpG sequences in the amplified regions of FBRS and REXO1L1 genes in MCF7 cells tend to be methylated.

Thus, the above primer sets can suitable used for quantitative PCR of methylated genomic DNA of MCF7 cells recovered by the MeDIP method.

Example 5

Investigation of Epitopes Recognized by the Present Monoclonal Antibodies

Epitopes which are recognized by the present monoclonal antibodies were investigated using 3MeCG and 3MeCT as antigens which were oligonucleotides containing methylated CpG and methylated CpT, respectively.
1. MeDIP Method With the similar procedures as Example 1, 6., genomic DNA (4 µg) extracted from MCF7 was used for preparation of a diluted solution of single-stranded DNA fragments, which was then subjected to the pre-clear treatment to give a DNA sample. To the obtained DNA sample was added 3MeCG which was denatured beforehand by heating at 95° C. for 10 minutes and quenching at 4° C. to obtain a 3MeCG sample. The sequence of 3MeCG is as follows.
<3MeCG>

(SEQ ID NO: 11)
5'-CGAGGTCGACGGTATTGATm5cGAGTATCGATAGTm5cGATATCGAT

ATCGATATm5cGATATACAACGTCGTGACTGG-3'

(wherein "m5c" represents a 5-methyl cytosine).

A 3MeCT sample was prepared in the similar manner as the above preparation of the 3MeCG sample except that 3MeCT was used instead of 3MeCG. The sequence of 3MeCT is as follows.
<3MeCT>

(SEQ ID NO: 12)
5'-CGAGGTCGACGGTATTGATm5cTAGTATCGATAGTm5cTATATCGAT

ATCGATATm5cTATATACAACGTCGTGACTGG-3'

Monoclonal antibodies obtained from SCR2 and SCR3 and the anti-methylated cytidine antibody from Diagenode were respectively added to the 3MeCG and 3MeCT samples. These samples were rotated overnight at 4° C. for reaction between the antibody and the antigen before addition of Protein G Sepharose beads (GE Healthcare) followed by the similar procedures as Example 1, 6. to elute DNA from the collected beads and purify the DNA.
2. Quantitative PCR In order to evaluate the recovery amount of the methylated DNA obtained by the MeDIP method, quantitative PCR was carried out.
(i) Preparation of PCR Reactions The similar reaction solution (25 µl) as Example 2 was prepared.

The primer set for methylated DNA detection included the primers having the sequences SEQ ID NO: 12 and SEQ ID NO: 13 shown below. This primer set can specifically amplify 3MeCG and 3MeCT.

```
F: 5'-CGAGGTCGACGGTAT-3'     (SEQ ID NO: 13)

R: 5'-CCAGTCACGACGTTGTA-3'   (SEQ ID NO: 14)
```

Quantitative PCR was carried out for the above reaction solutions with Mx3005P (Stratagene) under the following reaction conditions.
(ii) Reaction Conditions of Quantitative PCR One cycle of 95° C. for 10 minutes;

45 cycles of 95° C. for 30 seconds, 55° C. for 15 seconds and 72° C. for 30 seconds; and one cycle of 95° C. for 1 minute, 55° C. for 30 seconds and 95° C. for 30 seconds.

Serial dilutions of 3MeCG and 3MeCT were respectively prepared in order to prepare calibration curves. Quantitative PCR was carried out with these dilutions to prepare calibration curves. Based on the calibration curves, the copy numbers of the DNAs recovered by the MeDIP method were calculated based on the Ct values obtained in quantitative PCR, which were denoted as the recovery amount (copy) of methylated DNA.

Quantitative PCR was also carried out for the 3MeCG and 3MeCT samples prior to immunoprecipitation used in the MeDIP method and the copy numbers were calculated from the obtained Ct values, which were denoted as the recovery amount (copy) of Input DNA. From the calculated recovery amount (copy) of methylated DNA and the recovery amount (copy) of Input DNA, the recovery rate (copy/copy) was calculated according to the following equation (1):

[Recovery rate(copy/copy)]=[Recovery amount(copy) of methylated DNA]/[Recovery amount(copy) of Input DNA]   (1)

3. Results

Figure 5:
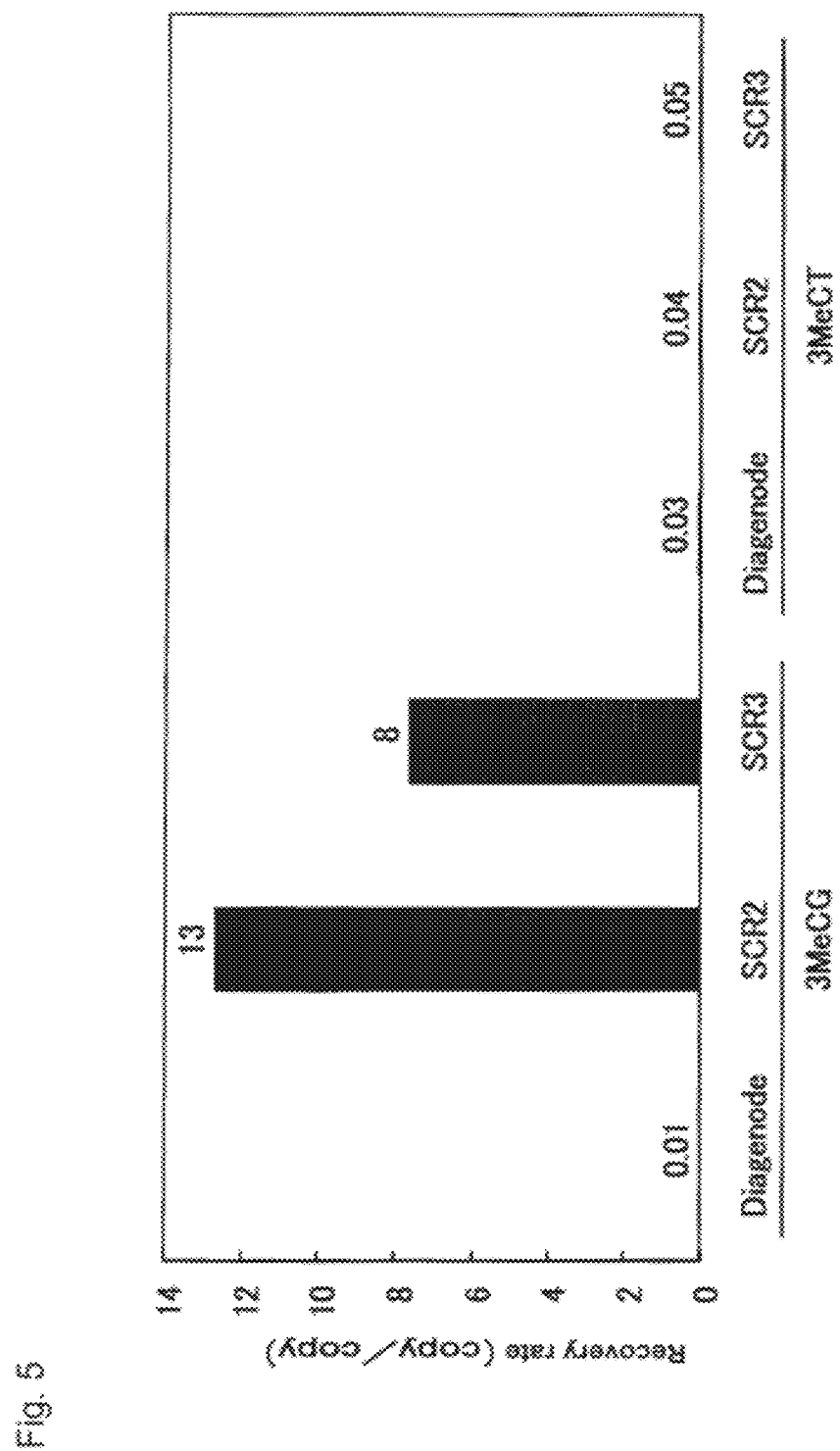
FIG. 5 is a bar graph showing the recovery rates of 3MeCG and 3MeCT recovered by the MeDIP method using the present monoclonal antibodies or the commercial antibody.

Table 4 and FIG. 5 show the recovery rates of 3MeCG and 3MeCT by the MeDIP method using monoclonal antibodies obtained from SCR2 and SCR3 and the anti-methylated cytidine antibody from Diagenode.

TABLE 4

|  | Antibody | Recovery rate (copy/copy) |
| --- | --- | --- |
| 3MeCG | Diagenode | 0.01 |
|  | SCR2 | 13 |
|  | SCR3 | 8 |
| 3MeCT | Diagenode | 0.03 |
|  | SCR2 | 0.04 |
|  | SCR3 | 0.05 |

It is found from Table 4 and FIG. 5 that recovery rates of 3MeCG and 3MeCT were not significantly different when the anti-methylated cytidine antibody from Diagenode was used in the MeDIP method.

On the other hand, the recovery rate of 3MeCG was significantly higher than that of 3MeCT when monoclonal antibodies obtained from SCR2 and SCR3 were respectively used in the MeDIP method. More specifically, the monoclonal antibody from SCR2 allowed 325 times higher recovery of 3MeCG than 3MeCT, and the monoclonal antibody from SCR3 allowed 160 times higher recovery of 3MeCG than 3MeCT.

These results showed that the monoclonal antibodies from SCR2 and SCR3 recognized methylated CpG sequences as epitopes.

The present application relates to Japanese Patent Application Nos. 2009-222893 and 2009-298213 filed on Sep. 28, 2009 and Dec. 28, 2009, respectively, whose claims, specifications, drawings and abstracts are incorporated herein by reference.

What is claimed is:

1. A hybridoma deposited at the National Institute of Technology and Evaluation under accession number NITE BP-810 (SCR1), NITE BP-805 (SCR2), NITE BP-811 (SCR3) or NITE BP-812 (SCR6).

2. A monoclonal antibody obtained from a hybridoma deposited at the National Institute of Technology and Evaluation under an accession number NITE BP-810 (SCR1), NITE BP-805 (SCR2), NITE BP-811 (SCR3) or NITE BP-812 (SCR6).

* * * * *